United States Patent
Kato et al.

(10) Patent No.: US 7,404,798 B2
(45) Date of Patent: Jul. 29, 2008

(54) ULTRASONIC DIAGNOSTIC APPARATUS AND ULTRASONIC DIAGNOSTIC APPARATUS CONTROL METHOD

(75) Inventors: Makoto Kato, Kyoto (JP); Masahiko Hashimoto, Shijonawate (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 321 days.

(21) Appl. No.: 10/519,885

(22) PCT Filed: Mar. 3, 2004

(86) PCT No.: PCT/JP2004/002667

§ 371 (c)(1),
(2), (4) Date: Dec. 30, 2004

(87) PCT Pub. No.: WO2004/089222

PCT Pub. Date: Oct. 21, 2004

(65) Prior Publication Data

US 2005/0240101 A1    Oct. 27, 2005

(30) Foreign Application Priority Data

Apr. 3, 2003    (JP)    ............................... 2003-100774

(51) Int. Cl.
*A61B 8/00*    (2006.01)
(52) U.S. Cl. ........................................ 600/450; 600/437
(58) Field of Classification Search ................ 600/437, 600/439, 486
See application file for complete search history.

(56) References Cited

U.S. PATENT DOCUMENTS

| | | | | |
|---|---|---|---|---|
| 5,411,028 A | * | 5/1995 | Bonnefous | ................... 600/454 |
| 5,494,037 A | * | 2/1996 | Banjanin et al. | ............. 600/455 |
| 5,544,656 A | * | 8/1996 | Pitsillides et al. | ............ 600/450 |
| 5,724,973 A | * | 3/1998 | Spratt | .......................... 600/449 |
| 5,830,131 A | * | 11/1998 | Caro et al. | ................... 600/300 |
| 5,840,028 A | | 11/1998 | Chubachi et al. | |
| 6,030,344 A | * | 2/2000 | Guracar et al. | .............. 600/447 |
| 6,036,643 A | | 3/2000 | Criton et al. | |

(Continued)

FOREIGN PATENT DOCUMENTS

JP        62-266040 A        11/1987

(Continued)

*Primary Examiner*—Eric F Winakur
*Assistant Examiner*—Helene Bor
(74) *Attorney, Agent, or Firm*—Panitch Schwarze Belisario & Nadel LLP

(57) ABSTRACT

An ultrasonic diagnostic apparatus is provided with an ultrasonic probe driving section 2, a receiving section 5 for amplifying an ultrasonic reflected wave, a phase detecting section 6 for phase-detecting the ultrasonic reflected wave, a velocity computing section 10 for obtaining the velocity of an object to be measured at a plurality of measuring positions on the object to be measured from a phase-detected signal, a computing section 10 for obtaining the deformation amount and/or elastic module between measuring positions of the object to be measured from the velocity, a fluid determining section 9 for determining a fluid portion in the object to be measured in accordance with the phase-detected signal, and an image data generating section 72 for two-dimensionally image-displaying the deformation amount and/or elastic module of the object to be measured in a region other than the fluid portion by using the information determined by the fluid determining section.

17 Claims, 8 Drawing Sheets

U.S. PATENT DOCUMENTS

| | | | |
|---|---|---|---|
| 6,132,373 A * | 10/2000 | Ito et al. | 600/437 |
| 6,193,669 B1 * | 2/2001 | Degany et al. | 600/486 |
| 6,200,268 B1 * | 3/2001 | Vince et al. | 600/443 |
| 6,264,609 B1 * | 7/2001 | Herrington et al. | 600/443 |
| 6,354,999 B1 * | 3/2002 | Dgany et al. | 600/486 |
| 6,398,732 B1 * | 6/2002 | Brock-Fisher et al. | 600/443 |
| 6,436,043 B2 * | 8/2002 | Bonnefous | 600/438 |
| 6,730,035 B2 * | 5/2004 | Stein | 600/449 |
| 6,817,982 B2 * | 11/2004 | Fritz et al. | 600/443 |
| 6,835,177 B2 * | 12/2004 | Fritz et al. | 600/443 |
| 6,852,083 B2 * | 2/2005 | Caro et al. | 600/485 |
| 6,875,176 B2 * | 4/2005 | Mourad et al. | 600/442 |
| 7,022,077 B2 * | 4/2006 | Mourad et al. | 600/449 |
| 7,041,060 B2 * | 5/2006 | Flaherty et al. | 600/485 |
| 2004/0034304 A1 * | 2/2004 | Sumi | 600/439 |
| 2007/0032726 A1 * | 2/2007 | Osaka et al. | 600/459 |

FOREIGN PATENT DOCUMENTS

| | | |
|---|---|---|
| JP | 09-051896 A | 2/1997 |
| JP | 10-005226 A1 | 1/1998 |
| JP | 11-089846 A | 4/1999 |
| JP | 2000-229078 A | 8/2000 |
| JP | 2001-037758 A | 2/2001 |
| JP | 2001-070305 A | 3/2001 |
| JP | 2001-292995 A | 10/2001 |

* cited by examiner

ULTRASONIC DIAGNOSTIC APPARATUS AND ULTRASONIC DIAGNOSTIC APPARATUS CONTROL METHOD

CROSS-REFERENCE TO RELATED APPLICATION

This application is a Section 371 of International Application No. PCT/JP2004/002667, filed Mar. 3, 2004, which was published in the Japanese language on Oct. 21, 2004, under International Publication No. WO 2004/089222 A1, the disclosure of which is incorporated herein by reference.

TECHNICAL FIELD

The present invention relates to an ultrasonic diagnostic apparatus, particularly to an ultrasonic diagnostic apparatus for performing tissue characterization in a living body and its control method.

BACKGROUND ART

The number of persons suffering from circulatory organ diseases such as myocardial infarction and cerebral infarction has been increased in recent years and it is a large problem to prevent and remedy these diseases.

Hardening of arteries deeply relates to the attack of myocardial infarction and cerebral infarction. Specifically, when atheroma is formed on an arterial wall or a new cell of an artery is formed due to various factors including a high blood pressure, the artery loses elasticity and becomes hard and fragile. Moreover, when a blood vessel is obstructed at the portion where the atheroma is formed or a blood vessel tissue covering the atheroma is broken, the atheroma leaks into a blood vessel, the artery is obstructed at another portion, or the portion where the artery is hardened is broken. Thereby, these diseases are caused. Therefore, diagnosis of hardening of arteries is important for prevention or remedy of these diseases.

Whether an artery is hardened has been diagnosed by directly observing a state of the inside of a blood vessel by a blood vessel catheter. However, this diagnosis has a problem that the burden of a patient is large because it is necessary to insert a blood vessel catheter into a blood vessel. Therefore, observation by a blood vessel catheter is used for a patient whose artery is exactly hardened to specify the place where the artery is hardened but this method is not used as an inspection for health care.

Measuring a cholesterol value which is a factor of hardening of arteries or measuring a blood pressure value is an inspection which can be easily performed because the burden to a patient is small. However, these values do not directly mean a degree that an artery is hardened.

Moreover, when it is possible to administer a curative medicine of hardening of arteries to a patient whose hardening of arteries is not greatly progressed, this exhibits an effect for medical treatment of hardening of arteries. However, when the hardening of arteries is progressed, it is said that it is difficult to completely cover hardened arteries though it is possible to restrain hardening of arteries by a curative medicine.

From this reason, a diagnostic method and a diagnostic apparatus are requested which do not apply much burden to a patient and diagnose the degree of hardening of arteries before hardening of arteries progresses.

An ultrasonic diagnostic apparatus has been known so far as a medical diagnostic apparatus which does not apply much burden to a patient. By using an ultrasonic diagnostic apparatus and thereby applying ultrasonic waves from the outside of a body, it is possible to obtain shape information, motion information, or quality information on the inside of a body without providing a pain for a patient.

Particularly when performing measurement by ultrasonic waves, it is possible to obtain the elastic modulus of an object to be measured because the motion information on the object to be measured is obtained from a transmutation value. That is, it is possible to obtain the elastic modulus of a blood vessel in a living body and directly know the degree of hardening of arteries. Moreover, because measurement can be made only by touching a patient with an ultrasonic probe, the burden to the patient decreases. Therefore, by using an ultrasonic diagnostic apparatus, it is possible to accurately diagnose hardening of arteries and it is expected to apply a medical inspection for prevention to a test subject without providing burden for the test subject.

However, an ultrasonic diagnostic apparatus having been used so far does not have a very high resolution of shape information or motion information as represented by an ultrasonic diagnostic apparatus for auscultating the cardiac sound of an unborn baby. Therefore, it is impossible to obtain the elastic modulus of a contracting artery in accordance with a heart beat. For example, there are many ultrasonic diagnostic apparatuses by which transmutation measurement of an object to be measured cannot sufficiently be performed like the ultrasonic diagnostic apparatus disclosed in Japanese Patent Laid-Open No. 62-266040.

It has been possible in recent years to improve the measurement accuracy of an ultrasonic diagnostic apparatus by leaps and bounds in accordance with the progress of electronics technique. Thereby, development of an ultrasonic diagnostic apparatus for measuring micro-movement of a living-body tissue has been progressed. For example, Patent Document 2 discloses an ultrasonic diagnostic apparatus for realizing high-accuracy phase tracking by using the amplitude and phase of a detection signal and deciding the instantaneous position of an object in accordance with a constrained least square method. This apparatus can measure the microvibration of a tissue greatly moved by a heart beat. According to Patent Document 2, micro-vibration up to hundreds of Hz on a great vibratory transmutation movement due to a heart beat having an amplitude of 10 mm or more can be measured at a preferable reproducibility even if a heart beat is repeated approx. 10 times.

The apparatus disclosed in Japanese Patent Laid-Open No. 10-5226 can measure high frequency components up to hundreds of Hz at a preferable reproducibility and obtain the elastic characteristic of a region having a diameter of 1 to 2 mm on cardiac muscle or artery by converging an ultrasonic beam. Moreover, it is reported that there is a superior characteristic that ultrasonic oscillation of the component of every time phase can be obtained in one heart beat and frequency spectrum of the oscillation can be analyzed.

Therefore, according to the ultrasonic diagnostic apparatus of this Japanese Patent Laid-Open No. 10-5226, it is expected that it is possible to prevent a disease due to hardening of arteries by checking a progress degree of hardening of arteries with time without providing burden for a test subject in a medical inspection. Moreover, by measuring the elastic characteristic in a micro-region of an artery, it is expected that it is possible to specify a portion at which ruptured blood vessel easily occurs and remedy the portion.

Motion information on living-body tissue measured by ultrasonic waves has been visualized so far by using an image display unit such as a monitor and thereby performing two-dimensional mapping. For example, a method is widely known in which a straight line drawn by brightness-modulating an ultrasonic incoming signal in accordance with an amplitude intensity is written in an image in accordance with scanning by an ultrasonic beam to display the tomogram of a two-dimensional living body in real time. This method is referred to as B-mode method, in which a difference between living-body tissues such as internal organs is displayed in accordance with its movement and a difference between brightnesses. Therefore, for example, it is possible to observe the shape of an unborn baby or find a bilestone. In the case of a conventional ultrasonic diagnostic apparatus not having a very high resolution of shape information or motion information, the above image display coincides with the purpose of the diagnosis.

However, in the case of an ultrasonic diagnostic apparatus having a high resolution using the technique disclosed in Japanese Patent Laid-Open No. 10-5226, it is possible to measure the motion information such as the elastic information on a blood vessel wall at a resolution of 1 to 2 mm. Therefore, a state in which blood moves through a blood vessel and a blood vessel wall performs a deformation amount is measured as a motion state nearby the blood vessel. In the case of the elastic characteristic to be image-displayed, the elastic characteristic of the blood in a blood vessel is shown in addition to the elastic characteristic of a blood vessel wall to be measured. As a result, the boundary between the blood vessel wall and the blood becomes unclear and it is difficult to accurately evaluate the elastic characteristic of the blood vessel wall. Particularly, it is very difficult to find regions different from each other in elastic characteristic in the blood vessel wall and specify a portion where hardening of arteries occurs by using the above display.

DISCLOSURE OF THE INVENTION

The present invention solves the above problems and provides an ultrasonic diagnostic apparatus and an ultrasonic diagnostic apparatus control method capable of conspicuously displaying the deformation amount and elastic modulus of a region adjacent to a fluid portion even if including the fluid portion in an object to be measured.

An ultrasonic diagnostic apparatus of the present invention includes an ultrasonic probe driving section which drives an ultrasonic probe for transmitting an ultrasonic transmission wave to an object to be measured including a fluid portion in which fluid moves, a receiving section which amplifies an ultrasonic reflected wave obtained when the ultrasonic transmission wave reflects from the object to be measured and received by the ultrasonic probe, a phase detecting section which phase-detects the ultrasonic reflected wave, a computing section which obtains the moving speed of the object to be measured at a plurality of measuring positions of the object to be measured in accordance with the phase-detected signal respectively and obtains deformation amounts and/or elastic moduli between the measuring positions of the object to be measured in accordance with the moving speed, a fluid determining section which determines the fluid portion in the object to be measured in accordance with the phase-detected signal, and an image data generating section which generates image data for two-dimensionally image-displaying the deformation amounts and/or elastic moduli of the object to be measured in a region other than the fluid portion by using the information which is determined by the fluid determining section.

In the case of a preferable embodiment, the fluid determining section determines the fluid portion in accordance with the Doppler method.

In the case of a preferable embodiment, an ultrasonic diagnostic apparatus further includes a filter section for dividing the phase-detected signal into a frequency component higher than a predetermined value and a frequency component equal to or lower than the predetermined value and selectively inputting signals having divided frequency components to the fluid determining section and the computing section.

In the case of a preferable embodiment, the ultrasonic probe driving section generates a first driving pulse suited to obtain the deformation amounts and/or elastic moduli of the object to be measured and a second driving pulse suited to determine a fluid portion in accordance with the Doppler method, the computing section obtains the deformation amounts and/or elastic moduli in accordance with a signal obtained by phase-detecting an ultrasonic reflected wave obtained from the first driving pulse, and the fluid determining section determines the fluid portion in accordance with a signal obtained by phase-detecting an ultrasonic reflected wave obtained from the second driving pulse.

In the case of a preferable embodiment, the image data generating section generates image data obtained by synthesizing a first image obtained by using gradation display or chroma display corresponding to the deformation amounts and/or elastic moduli between positions of the object to be measured and thereby two-dimensionally mapping the deformation amounts and/or elastic moduli and a second image obtained by displaying the fluid portion with a predetermined color and regions other than the fluid portion with colorless transparence.

In the case of a preferable embodiment, the image data generating section generates image data including a third image obtained by displaying the deformation amounts and/or elastic moduli at positions corresponding to the fluid portion with a predetermined color or colorless transparence and using gradation display or chroma display corresponding to the deformation amounts and/or elastic moduli at positions corresponding to a region other than the fluid portion and thereby two-dimensionally mapping the deformation amounts and/or elastic moduli.

In the case of a preferable embodiment, the ultrasonic diagnostic apparatus further includes an envelop detecting section for envelop-detecting the ultrasonic reflected wave and an amplifying section for logarithm-amplifying an envelop-detected signal and the image data generating section generates image data obtained by synthesizing the B-mode image generated in accordance with a signal obtained from the amplifying section with the first and second image or the third image.

In the case of a preferable embodiment, the ultrasonic probe driving section further generates a third driving pulse suited to generate a B-mode image and the envelop detecting section envelop-detects an ultrasonic reflected wave obtained from the third driving pulse.

In the case of a preferable embodiment, the ultrasonic diagnostic apparatus further includes a display section for displaying an image in accordance with image data output from the image data generating section.

Moreover, an ultrasonic diagnostic apparatus control method of the present invention is a control method of an ultrasonic diagnostic apparatus having a transmitting/receiving section, a phase detecting section for phase-detecting a received ultrasonic wave, and a computing section for computing deformation amounts and/or elastic moduli in accordance with the phase-detected ultrasonic wave, which includes a step (A) of transmitting an ultrasonic wave to an object to be measured including a fluid portion in which fluid moves and receiving an ultrasonic reflected wave obtained when the ultrasonic wave reflects from the object to be measured, a step (B) of phase-detecting the ultrasonic reflected wave, a step (C) of obtaining the velocity of the object to be measured at a plurality of measuring positions of the object to be measured in accordance with the phase-detected signal and obtaining the deformation amounts and/or elastic moduli between the measuring positions of the object to be measured in accordance with the velocity, a step (D) of determining the fluid portion in the object to be measured in accordance with the phase-detected signal, and a step (E) of using the information determined by the fluid determining section and thereby generating image data for two-dimensionally image-displaying the deformation amounts and/or elastic moduli of the object to be measured in a region other than the fluid portion.

In the case of a preferable embodiment, the fluid portion is determined in accordance with the Doppler method in the step (D).

In the case of a preferable embodiment, the ultrasonic diagnostic control method further includes a step (F) of separating a frequency component higher than a predetermined value and a frequency component equal to or lower than the predetermined value from the phase-detected signal and executes the step (C) in accordance with signals having the separated frequency components.

In the case of a preferable embodiment, a first driving pulse suited to obtain the deformation amount and elastic modulus of the object to be measured and a second driving pulse suited to determine a fluid portion in accordance with the Doppler method are transmitted to the object to be measured in the step (A), the deformation amounts and/or elastic moduli are or is obtained in accordance with a signal obtained by phase-detecting an ultrasonic reflected wave obtained from the first driving pulse in the step (C), and the fluid portion is determined in accordance with a signal obtained by phase-detecting an ultrasonic reflected wave obtained from the second driving pulse in the step (D).

In the case of a preferable embodiment, the step (E) generates image data obtained by synthesizing a first image obtained by using gradation display or chroma display corresponding to the deformation amounts and/or elastic moduli and thereby two-dimensionally mapping the deformation amounts and/or elastic moduli with a second image displaying the fluid portion with a predetermined color and a region other than the fluid portion with colorless transparence.

In the case of a preferable embodiment, the step (E) displays the deformation amounts and/or elastic moduli at the position corresponding to the fluid portion with a predetermined color or colorless transparence and generates image data including a third image obtained by using gradation display or chroma display corresponding to the deformation amounts and/or elastic moduli and thereby two-dimensionally mapping the deformation amounts and/or elastic moduli.

In the case of a preferable embodiment, the ultrasonic diagnostic apparatus control method further includes a step (G) of envelop-detecting the ultrasonic reflected wave and logarithm-amplifying an envelop-detected signal and the step (E) generates image data obtained by synthesizing a B-mode image according to the logarithm-amplified signal with the first, second, or third image.

In the case of a preferable embodiment, a third driving pulse suited to generate a B-mode image is further generated in the step (A) and an ultrasonic reflected wave obtained from the third driving pulse is envelop-detected in the step (G).

BEST MODE FOR CARRYING OUT THE INVENTION

An ultrasonic diagnostic apparatus of the present invention measures the velocity of each portion of an object to be measured and a deformation amount and elastic module in each micro-region. However, the object to be measured does not move. Because the ultrasonic diagnostic apparatus of the present invention is particularly suited to measure the elastic module of each portion of a living body and has a high spatial resolution, it can be preferably used to measure the deformation amount and elastic module of a blood vessel wall. The ultrasonic diagnostic apparatus of the present invention is described below by taking a case of measuring the deformation amount and elastic modulus of a blood vessel wall as an example.

At the vicinity of a blood vessel wall to be measured by using the ultrasonic diagnostic apparatus of the present invention, the blood vessel wall specifies a flow channel through which blood flows and blood moves along the flow channel. Therefore, when measuring the deformation amount and elastic module nearby the blood vessel wall and displaying an image, the elastic characteristic of blood adjacent to the blood vessel wall is displayed, the boundary between the blood vessel wall and blood becomes unclear, and it is difficult to accurately evaluate the elastic characteristic of the blood vessel wall.

To solve this problem, the ultrasonic diagnostic apparatus of the present invention does not display the motion characteristic of blood when evaluating the motion characteristic of a blood vessel wall. Specifically, the ultrasonic diagnostic apparatus determines a fluid portion which is moving blood and specifies the fluid portion in an object to be measured or obtains positional information. Moreover, when two-dimensionally mapping the motion characteristic nearby the blood vessel wall obtained by transmitting/receiving an ultrasonic wave and generating the data to be image-displayed, the ultrasonic diagnostic apparatus does not display the motion characteristic at the fluid portion by using the information on a specified fluid portion.

First Embodiment

Figure 1:
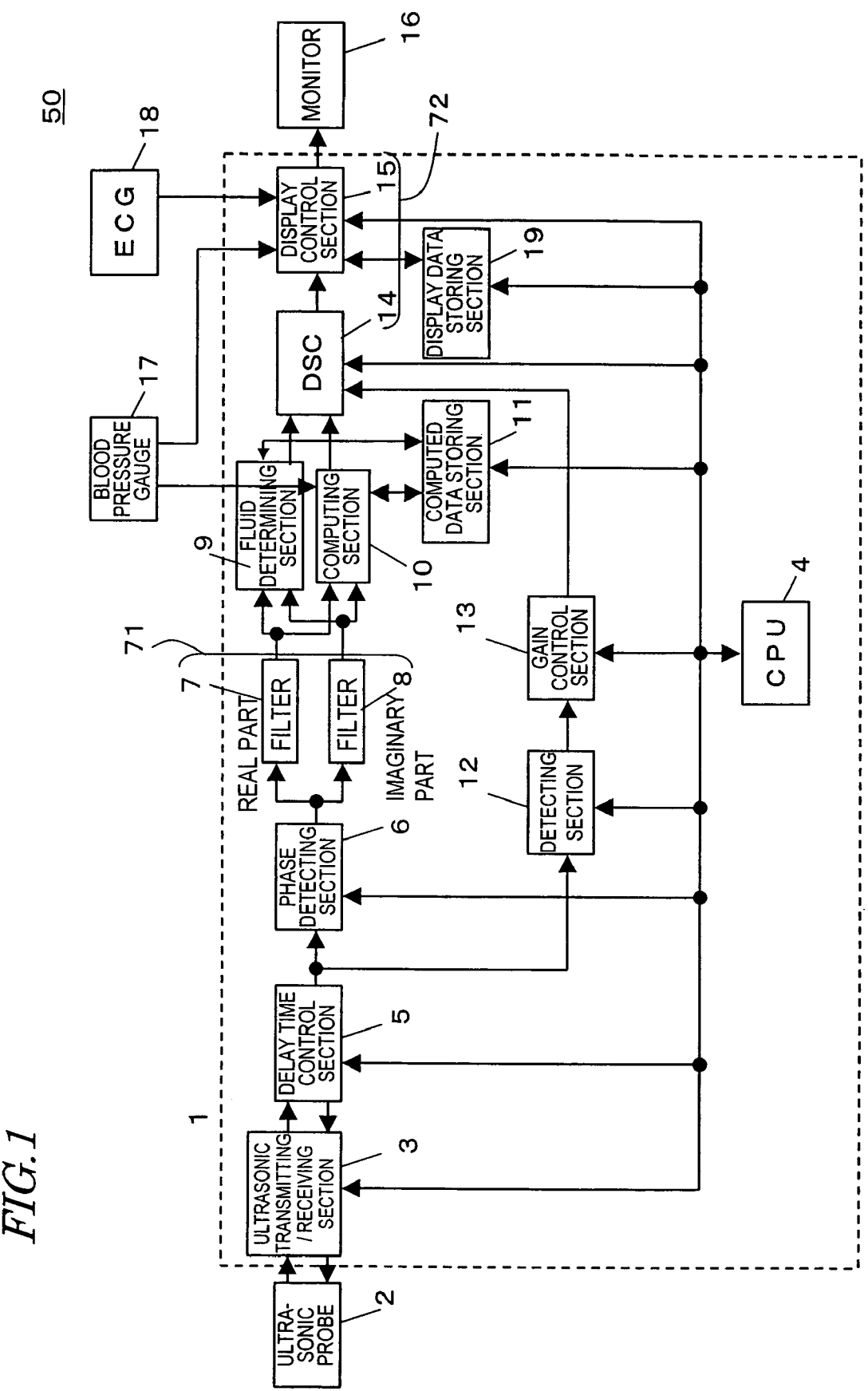
FIG. 1 is a block diagram showing a configuration of first embodiment of an ultrasonic diagnostic apparatus of the present invention.

First embodiment of the present invention is schematically described below. FIG. 1 is a block diagram showing a configuration of an ultrasonic diagnostic apparatus 50. The ultrasonic diagnostic apparatus 50 has an ultrasonic diagnostic apparatus body 1, an ultrasonic probe 2, and a monitor 16. Moreover, a blood pressure gauge 17 and an ECG (electrocardiograph) 18 are connected to the ultrasonic diagnostic apparatus body 1.

The ultrasonic diagnostic apparatus body 1 includes an ultrasonic transmitting/receiving section 3, CPU 4, delay time control section 5, phase detecting section 6, and filter section 71.

The ultrasonic probe 2 is connected to the ultrasonic transmitting/receiving section 3 of the ultrasonic diagnostic apparatus body 1 to transmit/receive an ultrasonic wave to and from a living body which is an object to be measured. The object to be measured includes a fluid portion which is blood flowing through a blood vessel. The ultrasonic probe 2 has a plurality of ultrasonic transducers (ultrasonic transducer group) arranged like an array.

The ultrasonic transmitting/receiving section 3 is constituted by using an electronic component and the like, which includes a driving circuit for driving the ultrasonic probe 2 serving as an ultrasonic probe driving section and a receiving circuit serving as a receiving section for amplifying an ultrasonic reflected wave. The ultrasonic probe driving circuit supplies a predetermined driving pulse signal to the ultrasonic probe 2 in accordance with the control by the CPU 4 for controlling the whole of the ultrasonic diagnostic apparatus body 1. An ultrasonic transmission wave transmitted from the ultrasonic probe 2 in accordance with a driving pulse reflects at a living body and a generated ultrasonic reflected wave is received by the ultrasonic probe 2. The ultrasonic reflected wave received by the ultrasonic probe 2 is amplified in the receiving circuit. The ultrasonic transmitting/receiving section 3 also includes an A/D conversion circuit and the ultrasonic reflected wave amplified in the receiving circuit is converted into a digital signal.

The delay time control section 5 is connected to the ultrasonic transmitting/receiving section 3 to control the delay time of a driving pulse signal to be supplied to the ultrasonic vibration group of the ultrasonic probe 2 from the ultrasonic transmitting/receiving section 3. Thereby, directions and focus depths of the acoustic line of the ultrasonic beam of an ultrasonic transmission wave transmitted from the ultrasonic probe 2 are changed. Moreover, by controlling the delay time of the amplified ultrasonic reflected wave received by the ultrasonic probe 2 and amplified by the ultrasonic transmitting/receiving section 3, it is possible to change directions of the acoustic line of a received ultrasonic wave. An output of the delay time control section 5 is input to the phase detecting section 6.

As described below in detail, an ultrasonic wave to be transmitted/received by the ultrasonic transmitting/receiving section 3 is used to measure the elastic modulus of an object to be measured, determine a fluid portion by the Doppler method, and display a B-mode image. Therefore, the ultrasonic transmitting/receiving section 3 and delay time control section 5 transmit or receive an ultrasonic wave in accordance with one type of a driving pulse and a scanning method suitable for any one of these purposes. Particularly, it is important to obtain the elastic modulus of an object to be measured by using the ultrasonic diagnostic apparatus 50. Therefore, it is preferable to select a driving pulse, delay time, and scanning method most suitable for measurement of an elastic modulus.

The phase detecting section 6 phase-detects a received reflected wave signal delay-controlled by the delay time control section 5 and divides the signal into a real part and an imaginary part. It is also allowed to set a filter for removing a high-frequency component to the output section of the phase detecting section 6 in order to remove the high-frequency component due to aliasing. It is allowed to constitute the delay time control section 5 and phase detecting section 6 by software or hardware. Divided real-part signal and imaginary-part signal are input to the filter section 71. The filter section 71 includes a first filter 7 for dividing the divided real-part signal into a frequency component higher than a predetermined value and a frequency component equal to or lower than the predetermined value and a second filter 8 for dividing the divided imaginary-part signal into a frequency component higher than a predetermined value and a frequency component equal to or lower than the predetermined value. The first filter 7 and the second filter 8 are respectively constituted by a DSP (Digital Signal Processor) and basically have the same function though they are different in cutoff frequency or pass band.

Figure 2:
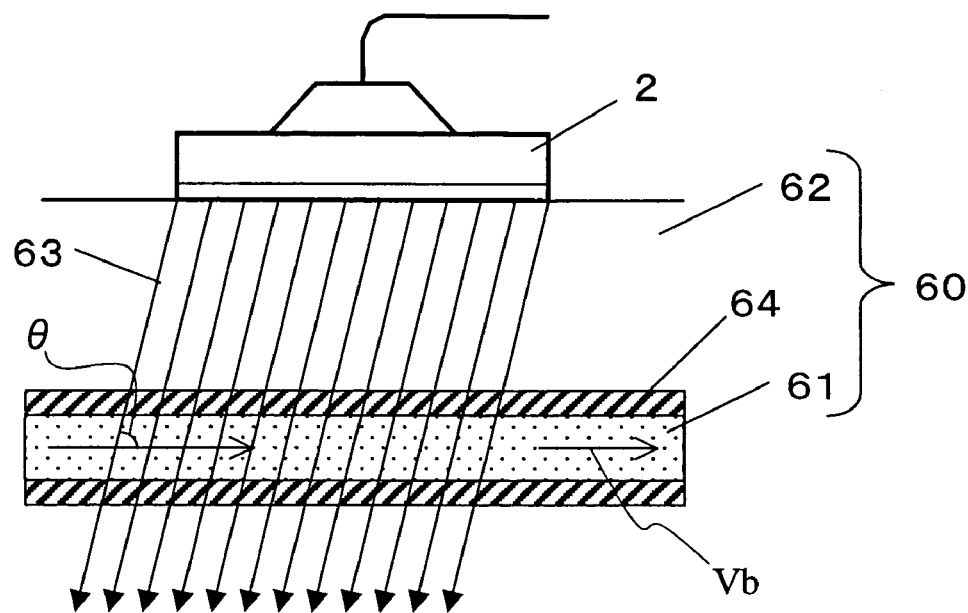
FIG. 2 is a schematic view for explaining a relation between ultrasonic beams and fluid moving directions.
Figure 3:
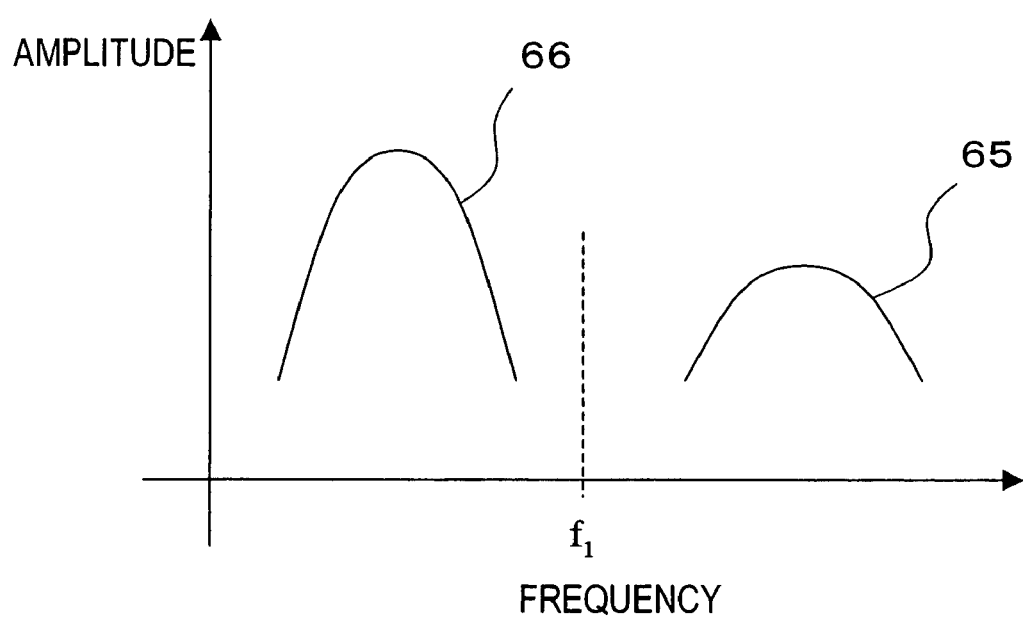
FIG. 3 is a schematic graph for explaining a Doppler shift.

The function of the filter section 71 is further described below by referring to FIGS. 2 and 3. FIG. 2 schematically shows a state of transmitting an ultrasonic wave to a living body 60 which is an object to be measured by using the ultrasonic diagnostic apparatus 50 of the present invention. The living body 60 includes a blood vessel wall 64, a fluid portion 61 which is blood flowing through a flow channel specified by the blood vessel wall 64, and a living-body tissue 62 other than a blood vessel. The fluid moves in the arrow direction at a speed of vb. The blood vessel wall 64 performs a deformation amount but the living-body tissue 62 hardly moves.

An ultrasonic wave is transmitted to an object to be measured so that an ultrasonic beam 63 reaches the upstream side of the fluid 61 at an acute angle θ from the traveling direction of the fluid by bringing the ultrasonic probe 2 into close contact with the surface of the living body 60. In this case, an ultrasonic wave reflected from the fluid 61 shifts to the high-frequency side due to the Doppler effect. However, because the blood vessel wall 64 and living-body tissue 62 hardly move, the shift of a frequency due to the Doppler effect is small. Therefore, as shown in FIG. 3, an ultrasonic reflected wave 65 obtained from the fluid 61 shifts to the high-frequency side compared to the case of an ultrasonic reflected wave 66 obtained from the blood vessel wall 64 and living-body tissue 62. By dividing a received ultrasonic reflected wave into a frequency component higher than a frequency f1 and a frequency component equal to or lower than the frequency f1 in the filter section 71, it is possible to separate a signal component by the fluid 61 from the received ultrasonic reflected wave.

Figure 4:
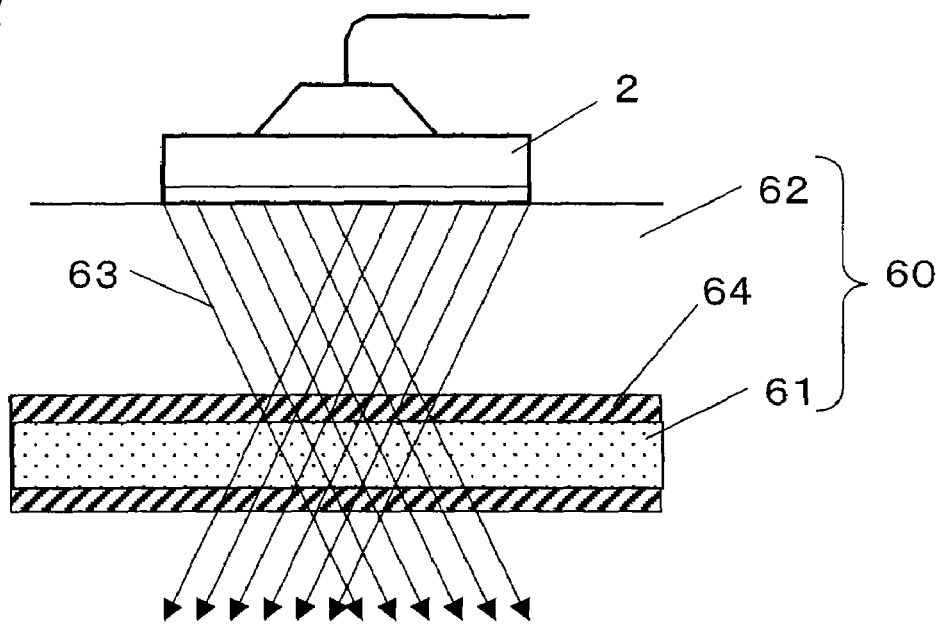
FIG. 4 is another schematic view showing a relation between ultrasonic beams and fluid moving directions.

When the ultrasonic reflected wave 65 obtained from the fluid 61 is overlapped with the ultrasonic reflected wave 66 obtained from the blood vessel wall 64 and living-body tissue 62 or it is difficult to separate the former from the latter. The angle θ of the ultrasonic beam 63 from the traveling direction of the fluid 61 is decreased by the delay time control section 5. Thereby, it is possible to increase the Doppler shift of an ultrasonic reflected wave obtained from the fluid 61. Moreover, as shown in FIG. 4, it is allowed to group the ultrasonic transducer group of the ultrasonic probe 2 so that directions emitted by the ultrasonic beam 63 differ.

The direction of Doppler-shifts in which a reflected wave obtained from the fluid 61 depends on the direction of the ultrasonic beam 63 to the traveling direction of the fluid 61. When the ultrasonic beam 63 reaches the downstream side of the fluid 61 and an ultrasonic wave is transmitted to an object to be measured so as to form an obtuse angle θ from the traveling direction of the fluid, a reflected wave obtained from the fluid 61 moves to the low-frequency side. That is, the ultrasonic reflected wave 65 obtained from the fluid 61 shifts to the low-frequency side compared to the case of the ultrasonic reflected wave 66 obtained from the blood vessel wall 64 and living-body tissue 62.

Therefore, the first filter 7 of the filter section 71 divides the real-part signal divided in the phase detecting section into a signal component having a large Doppler shift and a signal component having a small Doppler shift and the second filter 8 divides the imaginary-part signal divided in the phase detecting section into a signal component having a large Doppler shift and a signal component having a small Doppler shift.

The ultrasonic diagnostic apparatus body 1 further includes a fluid determining section 9, computing section 10, computed data storing section 11, image data generating section 72, and display data storing section 19. The fluid determining section 9, computing section 10, computed data storing section 11, and display data storing section 19 are constituted by using software or hardware and the image data generating section 72 is constituted by a circuit using an electronic component. By these configurations, a fluid portion in a region to be measured is determined in accordance with a phase-detected signal and the velocity and positional displacement value of a living-body tissue serving as an object are computed.

Specifically, the fluid determining section 9 receives a signal component having a large Doppler shift in the real-part signal and imaginary-part signal divided in the phase detecting section 6 from the first filter 7 and the second filter 8 of the filter section 71. Moreover, a fluid portion in a region to be measured is determined by the generally-used Doppler method to determine at least where the fluid portion is present. For example, it is allowed to obtain a flow rate at each position in a region to be measured by using the color Doppler method or specify the fluid portion in the region to be measured in accordance with the amplitude information by the power Doppler method. The positional information on the obtained fluid portion is sent to the image data generating section 72.

The computing section 10 receives a signal component having a small Doppler shift in the real-part signal and imaginary-part signal divided in the phase detecting section 6 from the first filter 7 and second filter 8 of the filter section 71. The computing section 10 includes a velocity computing section, position computing section, deformation amount computing section, and elastic modulus computing section. The velocity computing section of the computing section 10 obtains the velocity of a living-body tissue at a plurality of measuring positions in accordance with a received signal. The position computing section obtains a positional displacement amount by integrating a velocity. The deformation amount computing section obtains the deformation amount of a living body between measuring positions from the obtained positional displacement amount. Moreover, the elastic modulus computing section obtains the elastic modulus of a purposed tissue by using the data for a minimum blood pressure value and maximum blood pressure value input from the blood pressure gauge 17. An output of the computing section 10 is input to the image data generating section 72.

The computed data storing section 11 receives a phase-detected signal to be input to the fluid determining section 9 and computing section 10 or the positional information on a fluid portion obtained by the fluid determining section 9 and the velocity, positional displacement amount, deformation amount, or elastic modulus obtained by the computing section 10 from the fluid determining section 9 and computing section 10 to store them. Even if the computed data storing section 11 does not store a deformation amount or elastic modulus, it is possible to obtain the positional information on a fluid portion and the deformation amount and elastic modulus between a plurality of measuring positions when the fluid determining section 9 and computing section 10 read and compute a phase-detected signal, velocity, and positional displacement amount again.

As shown in FIG. 1, the ultrasonic diagnostic apparatus body 1 further includes a detecting section 12 and gain control section 13. The detecting section 12 and gain control section 13 modulate a received reflected wave signal at a brightness corresponding to the amplitude intensity of the reflected wave signal. Specifically, the detecting section 12 envelop-detects a received reflected wave signal output from the delay time control section 5. The gain control section 13 amplifies a plurality of detected signals and outputs them to the image data generating section 72. It is allowed to constitute the detecting section 12 and gain control section 13 by software or hardware.

The image data generating section 72 includes a DSC (Digital Scan Converter) 14 and a display control section 15. The DSC 14 converts the deformation amounts and/or elastic moduli obtained by the computing section 10 into two-dimensional mapping data. Moreover, the section 72 coverts at least the positional information on a fluid portion obtained from the fluid determining section 9 into a two-dimensional image. When the fluid determining section 9 uses the color Doppler method, it is allowed to generate a color flow image colored in accordance with the moving direction and flow rate of the fluid. Moreover, when using the power Doppler method, it is allowed to generate a gradation (brightness) image corresponding to the flow rate. A signal output from the gain control section 13 is converted into the data for a B-mode image. An output for the DSC 14 is input to the display control section 15.

The display control section 15 synthesizes these image data values output from the DSC 14 and converts them into the image data to be displayed on the monitor 16. Moreover, the section 15 receives the minimum blood pressure value and maximum blood pressure value obtained from the blood pressure gauge 17 and the waveform signal of an electrocardiogram obtained from the ECG (electrocardiograph) 18, converts these signals into image data, and superimposes the image data on the image data sent from the DSC 11. In this case, as described below in detail, the data located at a fluid portion in the two-dimensional mapping data for deformation amounts and/or elastic moduli is displayed with a predetermined color which is not changed even by the passage of time by using the positional information on the fluid portion of an image obtained from the fluid determining section 9. An output for the display control section 15 is input to the monitor 16 and the monitor 16 displays the output. An output of the display control section 15 is also output to the display data storing section 19 and it is possible to store a dynamic image or static image at an optional timing in the display data storing section 19.

Then, operations of the ultrasonic diagnostic apparatus 50 are described below in detail. A plurality of driving pulse signals whose delay times are controlled by the delay time control section 5 are output from the ultrasonic transmitting/receiving section 3 and the ultrasonic probe 2 converts each driving pulse signal into an ultrasonic transmission wave and transmits the wave to a living body. An ultrasonic reflected wave obtained by being reflected from a living-body tissue is received by the ultrasonic probe 2 and converted into an electrical signal. A received reflected wave signal received by the ultrasonic transmitting/receiving section 3 is input to the phase detecting section 7 after passing through the delay time control section 5. The delay time control section 5 sets different delay-time data to each driving pulse signal so that an ultrasonic wave can be transmitted or received at a deflection angle different for each driving pulse signal.

The phase detecting section 6 phase-detects a received reflected wave signal and divides it into a real-part signal and an imaginary-part signal. The first filter 7 of the filter section 71 divides the real-part signal divided by the phase detecting section into a signal component having a large Doppler shift and a signal component having a small Doppler shift and the second filter 8 divides the imaginary-part signal divided by the phase detecting section into a signal component having a large Doppler shift and a signal component having a small Doppler shift.

The signal component having a large Doppler shift is input to the fluid determining section 9 and a fluid portion in a region to be measured is determined by the Doppler method to obtain at least the positional information on the fluid portion. The signal component having a small Doppler shift is input to the computing section 10.

Figure 5:
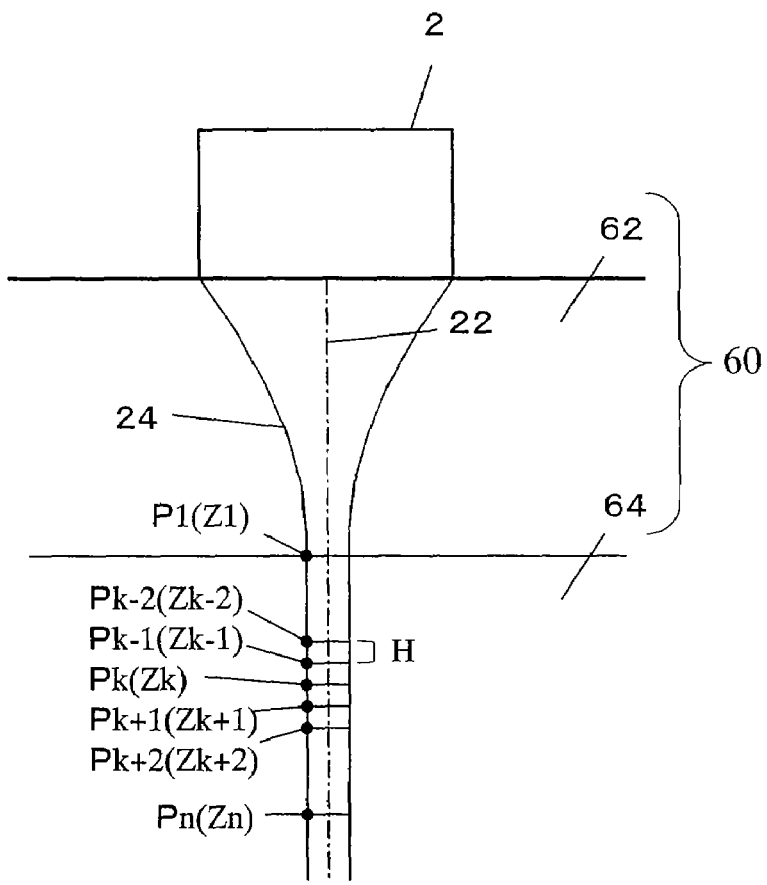
FIG. 5 is an illustration schematically showing an ultrasonic beam propagating through the blood vessel wall of a living body.

Computation of the positional displacement amount of a tissue in the computing section 10 is described below in detail by referring to FIG. 5. FIG. 5 schematically shows an ultrasonic beam 24 to be propagated through the living body 60. In FIG. 5, the blood vessel wall 64 and the living-body tissue 62 other than blood vessels are shown. An ultrasonic transmission wave transmitted from the ultrasonic probe 2 set to the surface of the living body 60 progresses through the living body 60. The ultrasonic transmission wave propagates through the living body 60 as the ultrasonic beam 24 having a finite width and some of ultrasonic waves reflected from or scattered by the living-body tissue 62 and blood vessel wall 64 return to the ultrasonic probe 2 in the course and are received as ultrasonic reflected waves. Each ultrasonic reflected wave is detected as a time-series signal $r(t)$. A reflected time-series signal obtained from a tissue closer to the ultrasonic probe 2 is located at a position closer to the origin on time axis. It is possible to control the width (beam diameter) of the ultrasonic beam 24 by changing delay times.

A plurality of measuring positions Pn (P1, P2, P3, Pk ... Pn, n is a natural number of 3 or more) in a blood vessel wall 64 located on an acoustic line 22 serving as the central axis of the ultrasonic beam are arranged as P1, P2, P3, Pk, ... Pn in order to close state to the ultrasonic probe 2 at a certain interval H. When assuming that the depth-directional coordinates using the surface of the living body 60 as the origin are Z1, Z2, Z3, Zk ... Zn, the reflection from the measuring position Pk is located at $t_k=2Z_k/c$ on the time axis. In this case, c denotes the sound speed of an ultrasonic wave in a living body. The reflected wave signal $r(t)$ is phase-detected by the phase detecting section 6 and the detected signal is divided into a real-part signal and an imaginary-part signal to pass the signals through the filter section 71. Under the restriction that amplitudes of the reflected wave signal $r(t)$ and a reflected wave signal $r(t+\Delta t)$ after a micro-time $\Delta t$ do not change but only the phase and reflection position change, the computing section 10 obtains a phase difference in accordance with the least square method so that the mean squared difference between waveforms of the reflected wave signals $r(t)$ and $r(t+\Delta t)$ becomes minimum. The velocity $V_n(t)$ of the measuring position Pn is obtained from the phase difference and the positional displacement amount $d_n(t)$ can be obtained by further integrating the velocity $V_n(t)$.

Figure 6:
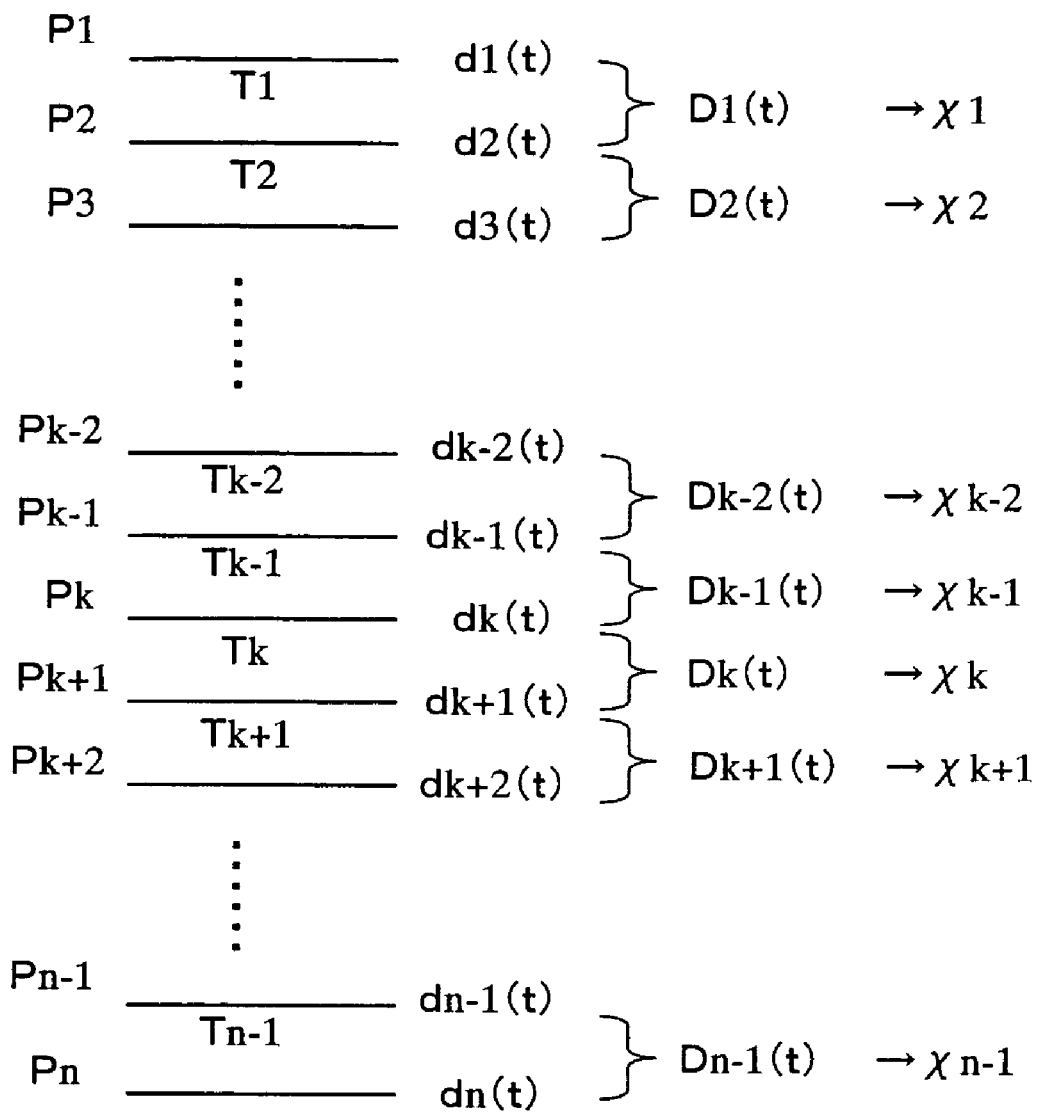
FIG. 6 is an illustration showing a relation between measuring positions and object tissues for obtaining elastic moduli.

Then, computation and display of an elastic modulus using these measured computing results are described below by referring to FIG. 6. FIG. 6 is an illustration showing a relation between the measuring position Pn and the purposed tissue Tn of elastic modulus computation. A purposed tissue Tk is located in a range surrounded by the adjacent measuring positions Pk and Pk+1 by having a thickness H. It is possible to set (n−1) purposed tissues T1 ... Tn−1 from the n measuring positions P1 ... Pn.

The thickness change amount $D_k(t)$ which is the deformation amount of the purposed tissue Tk is obtained as $D_k(t) = d_{k+1}(t) - d_k(t)$ from the displacement amounts $d_k(t)$ and $d_{k+1}(t)$ of the measuring positions Pk and Pk+1. The change of the thickness of the tissue Tk of the blood vessel wall 64 is caused by a change of blood pressure due to heart beat. Therefore, by using the thickness H (value at minimum blood pressure) of the purposed tissue Tk, the maximum value Dkmax of the thickness change amount $D_k(t)$ of a purposed tissue, and the pulse pressure B which is a difference between minimum blood pressure and maximum blood pressure, it is possible to obtain an elastic modulus $\chi_k$ which is a distortion factor of the purposed tissue Tk in accordance with $\chi_k = (B \times H)/D_{kmax}$. In this case, the elastic modulus $\chi_k$ is the elastic modulus in the radius direction of a blood vessel. Moreover, by controlling a delay time and scanning the deflection angle of an ultrasonic wave to be transmitted or received, it is possible to two-dimensional-mapping-display an elastic modulus at an optional cross section of the blood vessel wall 64. Because a minimum blood pressure value and maximum blood pressure value are updated in accordance with the pulsation period of a blood flow in a blood vessel, the elastic modulus $\chi_k$ is also updated. Therefore, an elastic modulus is updated almost in real time coinciding with a pulsation period.

Moreover, because a circumferential elastic modulus is also present in a blood vessel wall, it is allowed to obtain a circumferential elastic modulus of the blood vessel wall instead of or together with a radius-directional elastic modulus of the blood vessel wall. By obtaining an elastic modulus of a blood vessel wall in different directions, it is possible to more minutely diagnose hardening of arteries.

Then, generation of image data by the image data generating section 72 is described below. As described above, the DSC 14 of the image data generating section 72 converts the elastic modulus obtained by the computing section 10 into two-dimensional mapping data. It is also allowed to display a deformation amount instead of the elastic modulus or alternately display the elastic modulus and deformation amount. It is also allowed to generate two-dimensional mapping data for the both. In the case of two-dimensional mapping display, it is possible to display a gradation according to a color in which brightnesses are distributed or display a chroma obtained by relating the chroma to the magnitude of an elastic modulus. For example, it is possible to display a portion having a large elastic modulus and a portion having a small elastic modulus with blue and red and a portion having the middle value of the elastic modulus with an intermediate color between blue and red. It is also allowed that a user can freely select a combination of hues.

Moreover, the positional information on at least a fluid portion obtained from the fluid determining section 9 is converted into a two-dimensional image. As described above, it is also allowed to chroma-display the fluid portion correspondingly to a moving direction and a flow rate in accordance with the color Doppler method or gradation-display the fluid portion in accordance with the power Doppler method. A signal output from the gain control section 13 is converted into a B-mode image. An output of the DSC 14 is input to the display control section 15.

Figure 7:
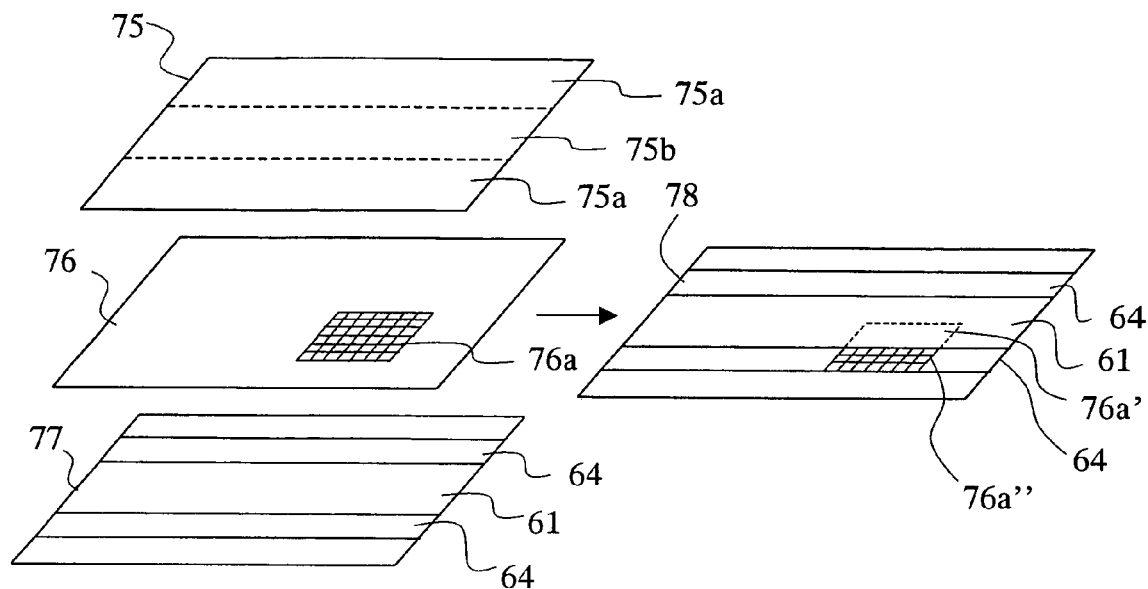
FIG. 7 is an illustration for explaining synthesis of images in an image data generating section.

The display control section 15 synthesizes these three images and generates image data. FIG. 7 schematically shows the synthesis of images in the display control section 15. In FIG. 7, two-dimensional image data 75 including the positional information on a fluid portion 75*b*, image data 76 including two-dimensional mapping data 76*a* for an elastic modulus, and B-mode image data 77 are schematically shown. The two-dimensional image data 75 includes the fluid portion 75*b* and other portion 75*a*. When obtaining the flow rate of the fluid at each measuring position in the fluid determining section 9, image data is generated in the DSC 14 so as to display a fluid portion with the gradation or chroma corresponding to the moving direction and the magnitude of the speed of the fluid portion. However, the display control section 15 applies conversion to the image data generated by the DSC 14 so as to display the fluid portion 75 with black or a color which is not changed in accordance with elapse of time and display the other portion 75*a* with colorless transparence in this two-dimensional image data 75.

As described above, the two-dimensional mapping data 76*a* for an elastic modulus is displayed with a gradation or chroma corresponding to the magnitude of the elastic modulus. The blood vessel wall 64 and the fluid portion 61 which is blood moving through a space specified by the blood vessel wall 64 are shown on the B-mode image 77.

As shown in FIG. 7, these three images are superimposed in the display control section 15 so that positions of objects to be measures are related to each other and image data 78 is generated. In this case, the two-dimensional mapping data 76*a* for an elastic module is prepared in a region covering the blood vessel wall 64 and fluid portion 61. However, because the fluid portion 75*b* is displayed with black, a portion 76*a'* to be superimposed with the fluid portion 75*b* of the two-dimensional mapping data 76*a* is displayed with black. That is, by masking a position corresponding to the fluid portion 75*b*, a two-dimensional map displayed with a gradation or chroma corresponding to an elastic modulus is displayed only in a region 76*a''* located at the blood vessel wall 64 for which display of an elastic modulus is requested in the synthesized image data 78 and the portion 76*a'* in the fluid (blood) 61 is displayed with black. Therefore, the elastic modulus of the blood vessel wall 64 can be easily seen and it is possible to easily find a portion whose elastic modulus is not normal in the blood vessel wall 64. Moreover, because the fluid 61 portion is always displayed with black even if the blood vessel wall 64 is moved or shifted due to the pulsation of a blood vessel, it is possible to visually easily trace the portion whose elastic modulus is not normal.

Thus, in the case of this embodiment, the positional information on a fluid portion is obtained from a signal component having a large Doppler shift obtained from the fluid portion so as not to display an elastic modulus on the fluid portion in accordance with the obtained positional information instead of removing the signal component having a large Doppler shift obtained from the fluid portion and simply displaying an elastic modulus obtained by using a remaining signal component with a two-dimensional map. By obtaining the positional information, it is possible to clarify the boundary between the fluid portion and a not-fluid portion (blood vessel wall) without being influenced by noises and clearly display a portion from which an elastic modulus can be correctly obtained.

In the case of the above image data generating section 72, a mask is prepared by using the data for the fluid determining section 9 to display only some of the two-dimensional mapping data for an elastic modulus with a gradation or chroma corresponding to the elastic modulus. However, it is also allowed to generate the two-dimensional mapping data for an elastic modulus in a region other than a fluid portion by directly using the positional information on the fluid determining section 9.

Figure 8:
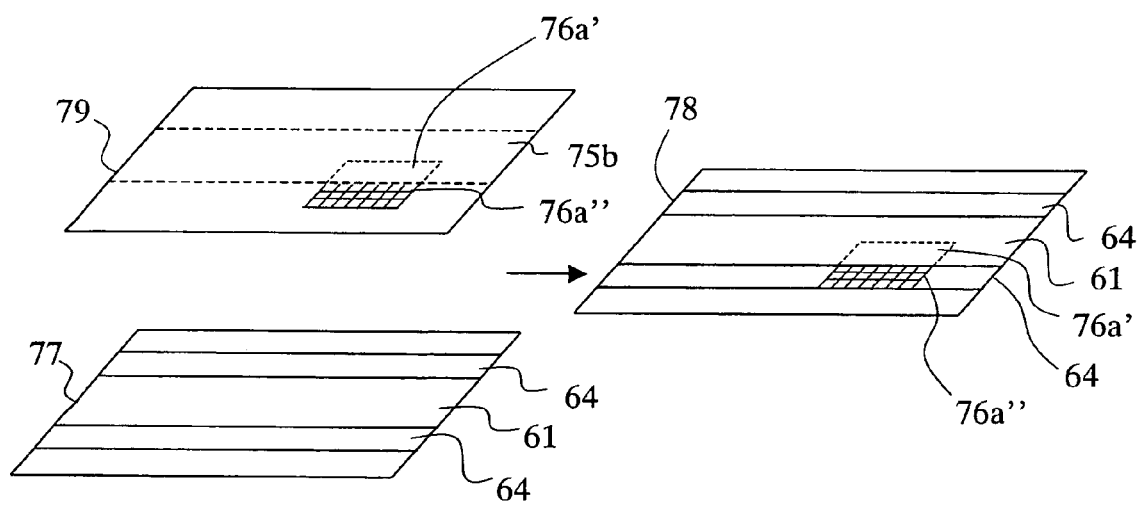
FIG. 8 is another illustration for explaining synthesis of images in the image data generating section.

For example, as shown in FIG. 8, when two-dimensional-mapping the elastic modulus obtained by the computing section 10 in the DSC 14, an elastic modulus is not mapped in the region 76*a'* corresponding to a fluid portion but the image data 79 obtained by mapping an elastic modulus only in the region 76" other than the fluid portion is generated by using the positional information on the fluid portion obtained from the fluid determining section 9. Or the image data 79 obtained by mapping an elastic modulus only in the region 76*a''* other than a fluid portion is generated so as to display the region 76*a'* corresponding to the fluid portion with black or colorless transparence. When synthesizing the image data 79 with the B-mode image data 77, the image data 78 displayed with a gradation or chroma corresponding to an elastic modulus is obtained only in the region 76" located at the blood vessel wall 64 for which display of an elastic modulus is requested. In this case, black or a B-mode image is displayed in a region corresponding to the fluid portion 76*a'*. By inputting the image data thus generated to the monitor 16, the elastic modulus of each portion of a living-body tissue is displayed so as to be easily seen.

It is allowed to display an image while collecting measurement data by transmitting an ultrasonic transmission wave toward a living body and receiving an ultrasonic reflected wave reflected from the living body. This is referred to as real-time display mode. Moreover, it is allowed to display an image by reading data from the computed data storing section 10 and generating the image data 78 in accordance with the above procedure after collecting measurement data. This is referred to as off-line display mode. It is allowed that an ultrasonic diagnostic apparatus has both the real-time display mode and the off-line display mode.

In this case, "real-time display" denotes sequentially displaying an image according to received ultrasonic reflected wave while an ultrasonic wave is transmitted or received by bringing the ultrasonic probe 2 into contact with a living body in order to obtain measurement data. It is allowed that the received ultrasonic reflected wave is instantaneously computed and an image is displayed substantially simultaneously with reception of the ultrasonic reflected wave or a time lag of several milliseconds to tens of milliseconds is present until an image is displayed after receiving the image because a lot of time is required for computation. The real-time display is suited to move a measurement region in accordance with a displayed image or search a purposed portion. Therefore, even if the time lag of the above time is present, it is possible to serve as "real-time display" as long as it is possible to stop the ultrasonic probe 2 to a living body during the time lag. Moreover, as long as the reception of an ultrasonic reflected wave and display of an image satisfy the above relation, it is allowed that various computed data values according to ultrasonic reflected waves are stored in a register or temporary-storage memory.

Furthermore, it is allowed to change a unit area for calculating an elastic modulus in a real-time display mode or off-line display mode. For example, to display elastic moduli of various portions of a living-body tissue in the real-time display mode, it is allowed to lower a spatial resolution by increasing the unit area for calculating an elastic modulus and to display elastic moduli of various portions of the living-body tissue in the off-line display mode, it is allowed to raise the spatial resolution by decreasing the unit area for calculating an elastic modulus. Thus, it is possible to perform stable image display not easily being influenced by a change of contact states between noise or ultrasonic probe and a living body in the real-time display mode and it becomes easy to move a measurement region and search a purposed portion by moving an ultrasonic probe in accordance with a displayed image. Moreover, even if a test subject performs an unnecessary operation, because a displayed image does not easily greatly change, it is not necessary to compel a strict stationary state from the test subject and it is possible to avoid the test subject from providing an unfavorable stress.

Furthermore, by lowering a deformation amount or the spatial resolution of an elastic modulus, it is possible to reduce the calculation quantity for image display in the real-time display mode. Therefore, it is possible to reduce the operation throughput requested for the CPU 4 of the ultrasonic diagnostic apparatus 50 and use the inexpensive CPU 4 having not having a very high operation throughput for the ultrasonic diagnostic apparatus 50. Thereby, it is possible to reduce the cost of an ultrasonic diagnostic apparatus. Furthermore, because only a small calculation quantity is necessary, it is possible to display an image immediately after receiving an ultrasonic reflected wave and perform real-time display having less time lag.

In the case of the above embodiment, the velocity and positional displacement amount of an issue to be measured from an ultrasonic reflected wave signal in accordance with the method disclosed in Patent Document 2. However, it is also allowed to obtain the velocity and positional displacement amount by using another method such as the zero cross detection method for an RF signal or tissue Doppler method.

Moreover, when a measurement area in the depth direction is narrow (short), it is possible to perform a measurement having a high resolution in may cases even if fixing the transmission focal depth and reception focal depth. When a measurement area in the depth direction is wide (long), it is possible to obtain an image having a high resolution by changing transmission focal depths or performing dynamic focusing at the time of reception.

Furthermore, when the fluid determining section 9 obtains the information on the moving speed and direction of fluid in accordance with the color Doppler method or power Doppler method and the DSC 14 converts the flow rate and moving direction of a fluid portion as image data in accordance with proper chroma display or gradation display, it is allowed to be able to superimpose the these image data values on B-mode image data and display them on a monitor.

Figure 9:
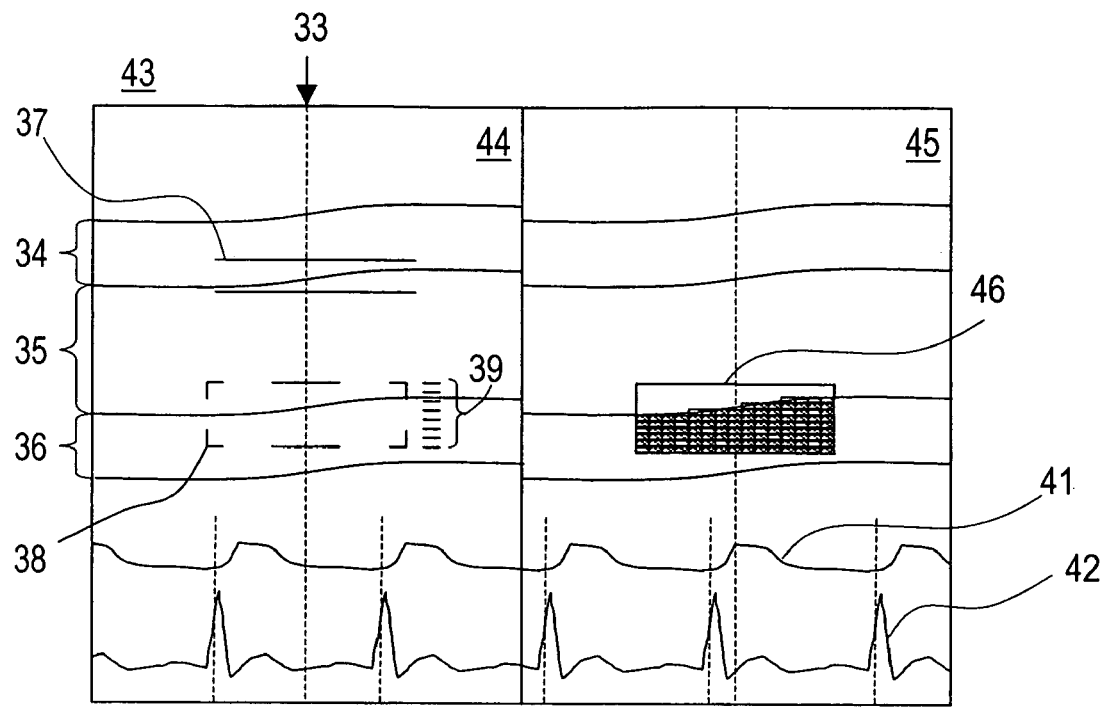
FIG. 9 is a schematic view showing an image when diagnosing a carotid artery.

An example of image display in the ultrasonic diagnostic apparatus 50 is described below. FIG. 9 is a schematic view of an image 43 showing a result of examining a carotid artery by using the ultrasonic diagnostic apparatus 50. In the case of this example, the elastic modulus of a blood vessel wall of the carotid artery is measured to search a micro calcified portion in the blood vessel wall. The calcification of the blood vessel wall is typical hardening of arteries.

FIG. 9 shows two-dimensional cross-section images 44 and 45 of a living body in accordance with the B mode in the left half and right half. The two-dimensional cross-section images 44 and 45 are cross-sections of a carotid artery of the living body in the longitudinal direction. The two-dimensional cross-section images 44 and 45 show a blood-vessel front wall 34, blood-vessel rear wall 36, and blood 35 serving as a fluid portion surrounded by the walls 34 and 36. When starting examination by bringing the ultrasonic probe 2 (FIG. 1) into contact with the living body, the two-dimensional cross-section images 44 and 45 are obtained. Moreover, the following are shown on the two-dimensional cross-section image 44: an acoustic line 33 (shown by a dotted line) of an ultrasonic beam used to photograph the two-dimensional cross-section images 44 and 45, a marker 37 (shown by two lines) for surrounding the boundary between the blood-vessel front wall 34 and blood 35, a region of inspection (also referred to as ROI) 38 (displaying positions of four corners), and a marker 39 showing positions for dividing the inside of the region of inspection 38 into seven equal portions in the depth direction. In the case of this example, the region of inspection 38 is displayed by 8 markers by dividing it into seven equal layers. However, actual positional displacement amount measurement is performed by 15 layers and therefore, elastic characteristics for 14 layers are computed.

An elastic characteristic map 46 obtaining elastic moduluses of various portions (radial elastic moduluses of a blood vessel) in the region of inspection 38 is superimposed on the two-dimensional cross-section image 45 as shown in FIG. 9 at the right. The position of the elastic characteristic map 46 corresponds to the region of inspection 38 in the two-dimensional cross-section image 44. The size of the region shown by the elastic characteristic map 46 is a transverse dimension of 10.0 mm and a longitudinal dimension of 3.5 mm and the size of each unit cell is a transverse dimension of 0.4 mm and a longitudinal dimension of 0.25 mm. Therefore, the region of inspection 38 is constituted by a unit cell divided into 14 rows and 25 columns.

Moreover, when measuring the elastic modulus of a blood vessel wall in the circumferential direction, it is necessary to obtain the inside diameter of a blood vessel. Therefore, the region of inspection 38 is set on the two-dimensional cross-section image 44 so that the boundary between the blood 35 and the blood-vessel rear wall 36 is included in the region of inspection 38. Similarly, the marker 37 is set so as to include the boundary between the blood 35 and the blood-vessel front wall 34. The CPU 4 of the ultrasonic diagnostic apparatus 50 obtains a position exceeding a site to which the bright change value or brightness change rate of B mode is previously set as the position of the boundary between the blood 35 and the blood-vessel front wall 34 and the position of the boundary between the blood 35 and the blood-vessel rear wall 36 and obtains the inside diameter of a blood vessel in accordance with the difference between these positions. A change of the obtained blood-vessel inside diameters is shown as a graph 41 at the lower portion of FIG. 9. Moreover, a waveform 42 of an electrocardiogram received from the ECG 18 is also displayed.

As described above, the region overlapped with the blood 35 is displayed with black in the elastic characteristic map 46. Therefore, the position of the boundary between the blood 35 and the blood-vessel rear wall 36 is demonstrated so that the position of a portion where the elastic modulus in the blood-vessel rear wall 36 is high is easily specified. In FIG. 9, the elastic characteristic map 46 is shown with a monochromatic tint corresponding to the value of the elastic modulus of each portion. However, it is also allowed to monochromatically display the two-dimensional cross-section images 44 and 45 and color-display the elastic characteristic map 46 by using a chroma corresponding to the value of an elastic modulus.

Figure 10:
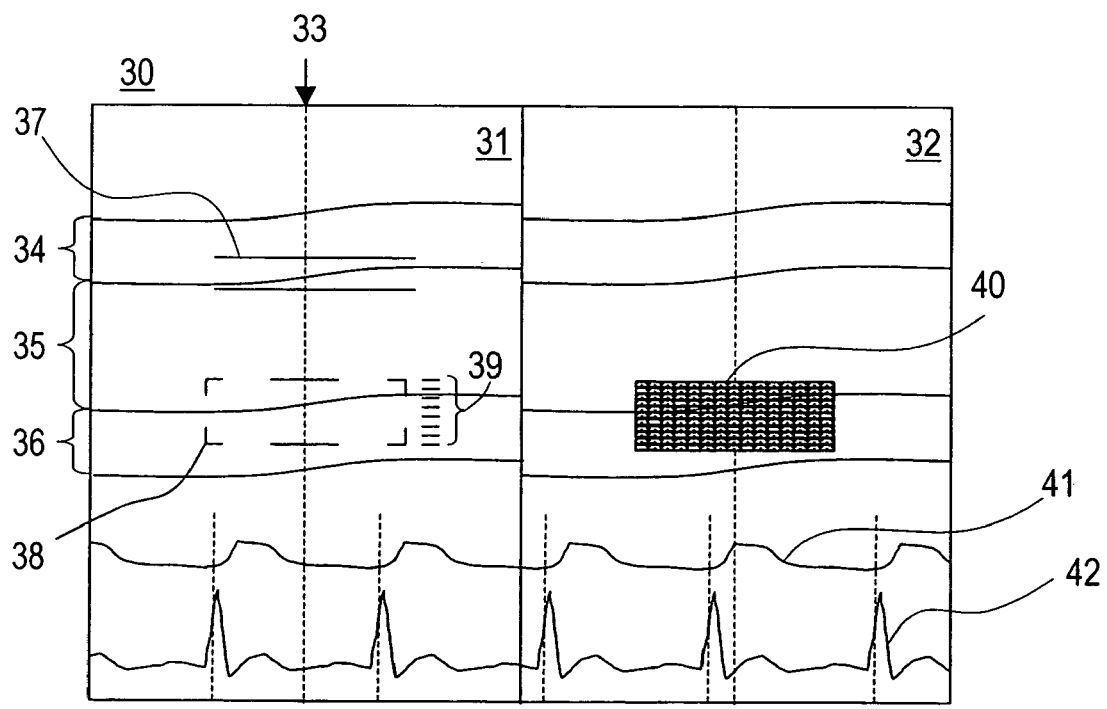
FIG. 10 is a schematic view showing an image also showing the elastic modulus of a fluid portion when diagnosing a carotid artery for comparison.

FIG. 10 shows a screen 30 when measuring an elastic modulus similarly to the case of FIG. 9 for comparison and showing the whole of the elastic characteristic map 40 with a gradation or chroma corresponding to the value of an elastic modulus. FIG. 10 shows two-dimensional cross-section images 31 and 32 of a living body in accordance with the B mode in the left half and right half. As shown in FIG. 10, in the elastic characteristic map 40, the elastic modules of a region corresponding to the blood 35 is also shown with a gradation or chroma in addition to a region corresponding to the blood-vessel rear wall 36 and the boundary between the blood-vessel rear wall 36 and the blood 35 is not clear. Therefore, a specific portion of the elastic modulus in the blood-vessel rear wall 36 cannot be easily specified.

Moreover, the elastic modulus of blood is unnecessary for measurement and the data obtained from an ultrasonic wave reflected from blood does not show a correct elastic modulus. Displaying an unnecessary and inaccurate blood-portion elastic modulus may cause misunderstanding of a test subject.

The two-dimensional cross-section images 44 and 45 can be updated in real time at a display speed of approx. 30 frames/sec because they are B-mode images. However, because calculation of an elastic characteristic is performed at a heat beam interval of a test subject, the elastic characteristic map 46 is updated by the heat beat interval (approx. 1 frame/sec) of the test subject. Therefore, it is allowed to display the two-dimensional cross-section images 44 and 45 while updating them at a display speed of approx. 30 frames/sec and display the elastic characteristic map 46 by updating it at the heart beat interval (approx. 1 frame/sec) of the test subject. However, the two-dimensional cross-section image 45 to be overlapped with the elastic characteristic map 46 can be easily seen by updating the image 45 synchronously with the map 46. Moreover, because the two-dimensional cross-section image 44 is frequently used to refer to a portion hidden by the elastic characteristic map 46 of the two-dimensional cross-section image 45, the two-dimensional cross-section image 44 can be also easily seen by updating it synchronously with the elastic characteristic map 46.

Second Embodiment

Second embodiment of an ultrasonic diagnostic apparatus of the present invention is described below. As described for the first embodiment in detail, an ultrasonic diagnostic apparatus of the present invention specifies a fluid portion by using the Doppler method and obtains a B-mode image in addition to measurement of an elastic modulus. The first embodiment controls a driving pulse used for these purposes in common by the ultrasonic transmitting section 3 and the delay time control section 5. However, measurement of an elastic modulus, specification of a fluid portion by the Doppler method, and obtainment of a B-mode image are achieved by applying a different signal processing to received ultrasonic reflection and therefore, a driving pulse for obtaining a best result and a scanning method do not always coincide with each other. Therefore, this embodiment uses a driving pulse and a scanning method optimum for each measurement.

Figure 11:
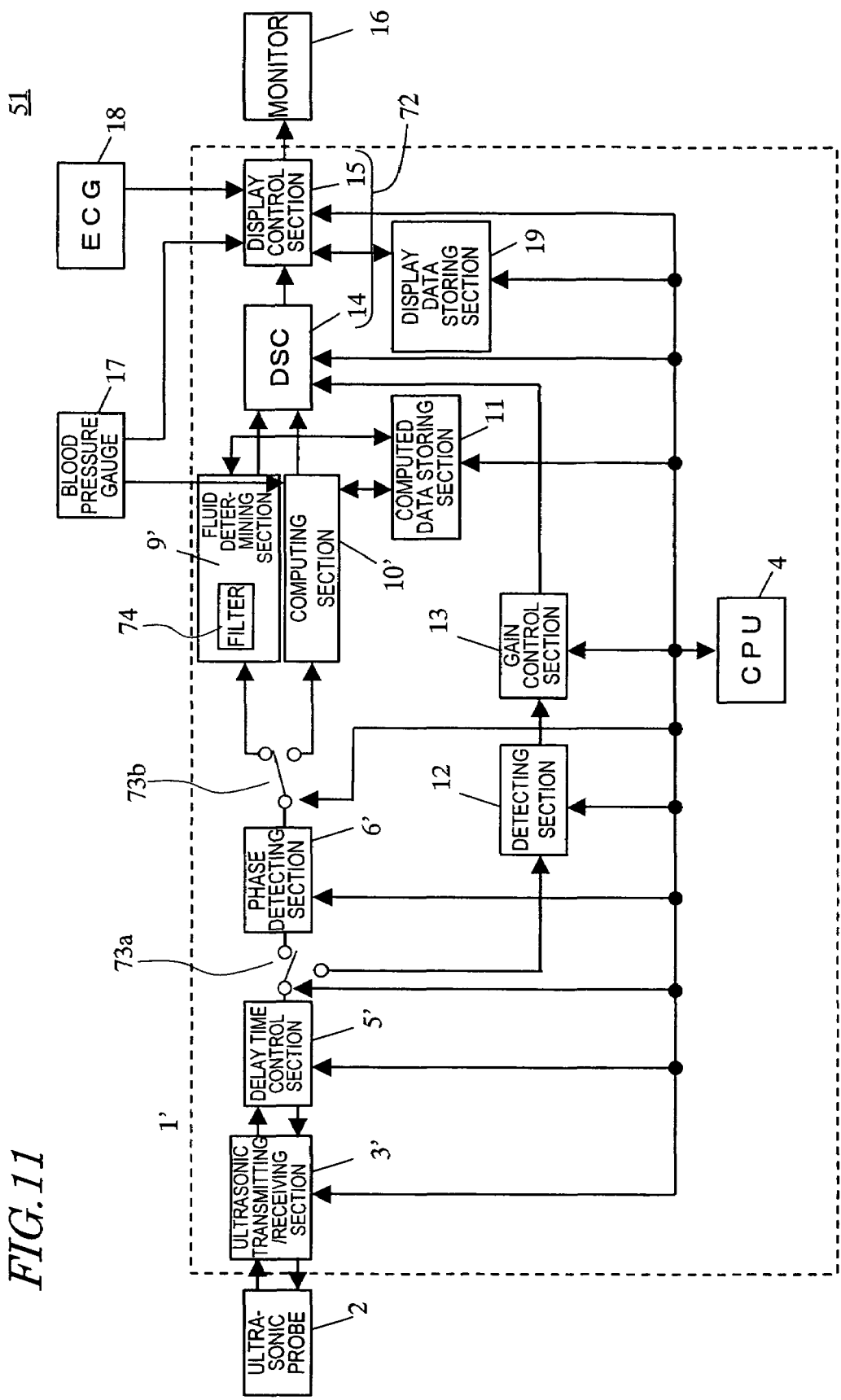
FIG. 11 is a block diagram showing a configuration of second embodiment of an ultrasonic diagnostic apparatus of the present invention.

As shown in FIG. 11, an ultrasonic diagnostic apparatus 51 is provided with an ultrasonic transmitting/receiving section 3', delay time control section 5', phase detecting section 6', fluid determining section 9', and computing section 10' instead of the ultrasonic transmitting/receiving section 3, delay time control section 5, phase detecting section 6, fluid determining section 9, and computing section 10 of the first embodiment. Moreover, the ultrasonic diagnostic apparatus 51 is provided with switch sections 73a and 73b.

Figure 12:
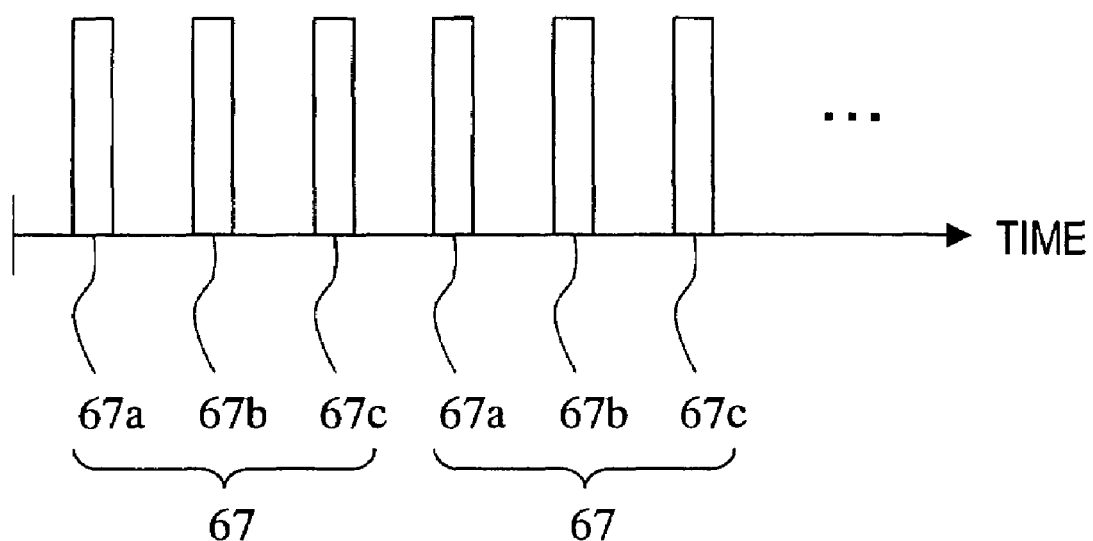
FIG. 12 is a schematic view for explaining an ultrasonic driving pulse string used for the ultrasonic diagnostic apparatus shown in FIG. 11.

FIG. 12 schematically shows a driving pulse group 67 output from the driving circuit of the ultrasonic transmitting/receiving section 3'. As shown in FIG. 12, the driving pulse group 67 output from the driving circuit includes driving pulses 67a, 67b, and 67c. Each of the driving pulses 67a to 67c is actually a burst wave including a plurality of pulses. The driving pulse 67a is optimized in order to obtain a B-mode image. Similarly, the driving pulses 67b and 67c are optimized so as to be able to measure an elastic modulus and specify a fluid portion in accordance with the Doppler method. Parameters to be optimized include a delay time and the number of pulses.

In the case of this embodiment, a driving pulse is transmitted in order of time series of the driving pulses 67a, 67b, and 67c to constitute the driving pulse group 67c. However, the sequence of driving pulses is not restricted to the above. For example, it is allowed to first transmit a driving pulse optimized to measure an elastic modulus.

Moreover, two driving pulse groups 67 are shown in FIG. 12. In the case of actual measurement, however, the driving pulses 67a, 67b, and 67c included in the driving pulse group 67 are used for generation of a B-mode image, measurement of an elastic modulus, and specification of the positional information on a fluid portion by repeatedly transmitting the driving pulse group 67. Therefore, it is allowed to change timings of the driving pulses 67a, 67b, and 67c in the driving pulse group 67 in accordance with a phase difference requested for each measurement. The ultrasonic transmitting/receiving section 3' and the delay time control section 5' repeat transmission and reception because the phases are adjusted so that the driving pulse groups 67 including these driving pulses respectively serve as an optimum scanning method.

The driving pulses 67a to 67c of each driving pulse group 67 are reflected from an object to be measured and it is necessary to apply different signal processing to obtained ultrasonic reflected waves. For this reason, the CPU 4 controls a signal processing route according to an ultrasonic reflected wave by using the switch sections 73a and 73b. Specifically, when the ultrasonic transmitting/receiving section 31 receives an ultrasonic reflected wave by the driving pulse 67a, an ultrasonic reflected wave signal output from the delay time control section 5' is input to the detecting section 12 by switching the switch section 73a. Moreover, a signal detected by the gain control section 13 is logarithm-amplified and output to the image data generating section 72.

However, when the ultrasonic transmitting/receiving section 3' receives ultrasonic reflected waves by the driving pulses 67b and 67c, an ultrasonic reflected wave signal output from the delay time control section 5' is output to the phase detecting section 6' by switching the switch section 73a. The phase detecting section 6' phase-detects an ultrasonic reflection signal as described for the first embodiment and divides the signal into a real-part signal and an imaginary-part signal. When obtained signals conform to the driving pulse 67b, the real-part signal and imaginary-part signal are output to the computing section 10' by the switch section 73b.

The computing section 10' obtains the velocity, positional displacement amount, deformation amount, and elastic modulus at each position of an object to be measured by using the received real-part signal and imaginary-part signal. The obtained data is sent to the image data generating section 72.

Moreover, when the real-part signal and imaginary-part signal obtained by the phase detecting section 6' conform to the driving pulse 67c, the real-part signal and imaginary-part signal are output to the fluid determining section 9' by the switch section 9'. The fluid determining section 9' includes a high-pass filter 74 to remove a signal component having a small Doppler shift from the real-part signal and imaginary-part signal. Moreover, the section 9' determines a fluid portion by using a signal component having a large Doppler shift. The positional information on the obtained fluid portion is output to the image data generating section 72.

The image data generating section 72 generates a two-dimensional mapping data for deformation amounts and/or elastic moduli by using the data for deformation amounts and/or elastic moduli received from the computing section 10' and the positional information on the fluid portion received from the fluid determining section 9'. In this case, the data located at the fluid portion in the two-dimensional mapping data is displayed with a predetermined color not changed even due to elapse of time by using the positional information on the fluid portion of an image obtained from the fluid determining section 9. Moreover, the image generating section 72 generates the data for a B-mode image in accordance with a signal obtained from the gain control section 13. The obtained B-mode image data and the two-dimensional mapping data for the deformation amount and/or elastic module are synthesized and displayed on the monitor 16. A specific generation method of these data values in the image data generating section 72 is the same as the case of the first embodiment.

The driving pulses 67a to 67c are not strictly transmitted at the same time. Therefore, the elastic module, position of the fluid portion, and B-mode image are obtained by being delayed by the time corresponding to intervals between the driving pulses 67a to 67c. However, the intervals between the driving pulses 67a to 67c are short and the moving distance of an object to be measured in the time can be ignored because it is very small. Therefore, it is possible to regard that the elastic modulus, position of the fluid portion, and B-mode image are substantially obtained at the same time and a shift to be perceived by a person does not occur between the two-dimensional map of the elastic modulus and the B-mode image displayed on the monitor.

According to this embodiment, measurement of an elastic modulus, specification of a fluid portion by the Doppler method, and obtainment of a B-mode image are performed by using an optimum driving pulse and a scanning method. Therefore, it is possible to obtain more accurate elastic modulus, positional information on a fluid portion, and detailed B-mode image. As a result, an image showing an object to be measured is more easily seen and it is easy to accurately specify unique portions of an expansion ratio and elastic modulus in the object to be measured.

This embodiment uses three types of driving pulses respectively suitable for measurement of an elastic modulus, specification of a fluid portion by the Doppler method, and obtainment of a B-mode image. It is allowed to use an exclusive driving pulse only for accurate measurement and use one type of a driving pulse for other measurements in common. For example, it is allowed to perform measurement by using a driving pulse group constituted by two types of driving pulses such as a driving pulse used for specification of a fluid portion by the Doppler method and obtainment of a B-mode image and a driving pulse used for measurement of an elastic modulus.

In the case of the first and second embodiments, a living body is used as an object to be measured and an ultrasonic diagnostic apparatus and an ultrasonic measuring method of the present invention are described. However, it is allowed to use an object other than a living body as the object to be measured. For example, it is possible to use the object other than a living body for mechanical vibration measurement of a pipe in a wall. Also in this case, it is possible to display the deformation amount and elastic module of only a pipe portion without displaying the deformation amount and elastic module of a fluid portion moving in a pipe. Therefore, it is possible to easily diagnose or inspect a pipe.

INDUSTRIAL APPLICABILITY

According to an ultrasonic diagnostic apparatus and its control method of the present invention, even if an object to be measured includes a fluid portion, it is possible to conspicuously image-display the deformation amount and elastic modulus only of a region adjacent to the fluid portion. Therefore, it is possible to improve the operability of a apparatus presently performing measurement and it is easy to find a unique portion of an expansion ratio or elastic modulus in an object to be measured.

An ultrasonic diagnostic apparatus and its control method of the present invention are suited to diagnose the elastic modulus of a living-body tissue. Moreover, they are suited to diagnose or inspect a pipe in a wall.

The invention claimed is:

1. An ultrasonic diagnostic apparatus comprising:
    an ultrasonic probe driving section for driving an ultrasonic probe for transmitting an ultrasonic transmission wave to an object to be measured including a blood vessel in which fluid moves and a fluid portion within the blood vessel, the fluid portion being an area;
    a receiving section for amplifying an ultrasonic reflected wave obtained when the ultrasonic transmission wave reflects from the object to be measured and is received by the ultrasonic probe;
    a phase detecting section for phase-detecting the ultrasonic reflected wave;
    a computing section for obtaining the velocities of the object to be measured at a plurality of measuring positions of the object to be measured from the phase-detected signal and obtaining the deformation amounts and/or elastic moduli in at least one micro-region from the velocities and in a radial direction of the blood vessel, the micro-region defined by a portion of the object to be measured between at least two of the measuring positions;
    a fluid determining section for determining the fluid portion in the object to be measured in accordance with the phase-detected signal; and
    an image data generating section for generating image data for two-dimensionally image-displaying the deformation amounts and/or elastic moduli of the object to be measured in a region other than the fluid portion by using the information determined by the fluid determining section.

2. The ultrasonic diagnostic apparatus according to claim 1, wherein the fluid determining section determines the fluid portion by the Doppler method.

3. The ultrasonic diagnostic apparatus according to claim 2, further comprising:
    a filter section for dividing the phase-detected signal into a frequency component higher than a predetermined value and a frequency component equal to or lower than the predetermined value and selectively inputting signals of the divided frequency components to the fluid determining section and the computing section.

4. The ultrasonic diagnostic apparatus according to claim 2, wherein:
    the ultrasonic probe driving section generates a first driving pulse suited to obtain the deformation amounts and/or elastic moduli of the object to be measured and a second driving pulse suited to determine the fluid portion by the Doppler method, the computing section obtains the deformation amounts and/or elastic moduli in accordance with a signal obtained by phase-detecting an ultrasonic reflected wave obtained by the first driving pulse, and the fluid determining section determines the fluid portion in accordance with a signal obtained by phase-detecting an ultrasonic reflected wave obtained by the second driving pulse.

5. The ultrasonic diagnostic apparatus according to claim 1, wherein the image data generating section generates image data obtained by synthesizing a first image obtained by using gradation display or chroma display corresponding to the deformation amounts and/or elastic moduli between the measuring positions and thereby two-dimensionally mapping the deformation amounts and/or elastic moduli and a second image obtained by displaying the fluid portion with a predetermined color and displaying a region other than the fluid portion with colorless transparence.

6. The ultrasonic diagnostic apparatus according to claim 5, further comprising:

an envelop detecting section for envelop-detecting the ultrasonic reflected wave and an amplifying section for logarithm-amplifying an envelop-detected signal, wherein the image data generating section generates image data obtained by synthesizing a B-mode image generated in accordance with a signal obtained from the amplifying section with the first and second images or the third image.

7. The ultrasonic diagnostic apparatus according to claim 6, wherein:

the ultrasonic probe driving section further generates a third driving pulse suited to generate a B-mode image, and the envelop detecting section envelop-detects an ultrasonic reflected wave obtained from the third driving pulse.

8. The ultrasonic diagnostic apparatus according to claim 1, wherein the image data generating section generates image data including a third image obtained by showing the deformation amounts and/or elastic moduli at positions corresponding to the fluid portion with a predetermined color or colorless transparence and two-dimensionally mapping the deformation amounts and/or elastic moduli at positions corresponding to a region other than the fluid portion by gradation display or chroma display corresponding to the deformation amounts and/or elastic moduli.

9. The ultrasonic diagnostic apparatus according to claim 1, further comprising a display section for displaying an image in accordance with image data output from the image data generating section.

10. A control method of an ultrasonic diagnostic apparatus having a transmitting/receiving section for transmitting/receiving an ultrasonic wave, a phase-detecting section for phase-detecting the received ultrasonic wave, and a computing section for computing a deformation amount and/or elastic modulus in accordance with the phase-detected ultrasonic wave, comprising the steps of:

(A) transmitting an ultrasonic wave to an object to be measured including a blood vessel in which fluid moves and a fluid portion within the blood vessel, the fluid portion being an area, and receiving an ultrasonic reflected wave obtained when the ultrasonic wave reflects from the object to be measured;

(B) phase-detecting the ultrasonic reflected wave;

(C) obtaining the velocities of the object to be measured at a plurality of measuring positions of the object to be measured in accordance with the phase-detected signal and obtaining the deformation amounts and/or elastic moduli in at least one micro-region from the velocities and in a radial direction of the blood vessel, the micro-region defined by a portion of the object to be measured between at least two of the measuring positions;

(D) determining the fluid portion in the object to be measured in accordance with the phase-detected signal; and (E) generating image data for two-dimensionally image-displaying the deformation amount and/or elastic modulus of the object to be measured in a region other than the fluid portion by using information of the fluid portion determined in step (D).

11. The ultrasonic diagnostic apparatus control method according to claim 10, wherein the fluid portion is determined in the step (D) in accordance with the Doppler method.

12. The ultrasonic diagnostic apparatus control method according to claim 11, further comprising:

(F) separating a frequency component higher than a predetermined value and a frequency component equal to or lower than the predetermined value from the phase-detected signal, wherein the step (C) is executed in accordance with signals of the separated frequency components.

13. The ultrasonic diagnostic apparatus control method according to claim 11, wherein:

a first driving pulse suited to obtain the deformation amounts and/or elastic moduli of the object to be measured and a second driving pulse suited to determine the fluid portion in accordance with the Doppler method are transmitted to the object to be measured in the step (A), the deformation amounts and/or elastic moduli are or is obtained from a signal obtained by phase-detecting an ultrasonic reflected wave obtained from the first driving pulse in the step (C), and the fluid portion is determined from a signal obtained by phase-detecting an ultrasonic reflected wave obtained from the second driving pulse in the step (D).

14. The ultrasonic diagnostic apparatus control method according to claim 10, wherein: the step (E) generates image data obtained by synthesizing a first image obtained by using gradation display or chroma display corresponding to the deformation amounts and/or elastic moduli and thereby two-dimensionally mapping the deformation amounts and/or elastic moduli with a second image obtained by displaying the fluid portion with a predetermined color and displaying a region other than the fluid portion with colorless transparence.

15. The ultrasonic diagnostic apparatus control method according to claim 14, further comprising a step (G) of envelop-detecting the ultrasonic reflected wave and logarithm-amplifying an envelop-detected signal, wherein the step (E) generates image data obtained by synthesizing a B-mode image according to the logarithm-amplified signal with the first and second images or the third image.

16. The ultrasonic diagnostic apparatus control method according to claim 15, wherein:

a third driving pulse suited to generate a B-mode image is further generated in the step (A), and an ultrasonic reflected wave obtained from the third driving pulse is envelop-detected in the step (G).

17. The ultrasonic diagnostic apparatus control method according to claim 10, wherein the step (E) generates image data obtained by displaying the deformation amounts and/or elastic moduli at positions corresponding to the fluid portion with a predetermined color or colorless transparence and using gradation display or chroma display corresponding to the deformation amounts and/or elastic moduli at positions corresponding to a region other than the fluid portion and thereby two-dimensionally mapping the deformation amounts and/or elastic moduli.

* * * * *